(12) United States Patent
Rubehn et al.

(10) Patent No.: US 10,369,355 B2
(45) Date of Patent: Aug. 6, 2019

(54) ACTIVE FIXATION OF NEURAL TISSUE ELECTRODES

(71) Applicant: MED-EL Elektromedizinische Geraete GmbH, Innsbruck (AT)

(72) Inventors: Birthe Rubehn, Innsbruck (AT); William Denny, Innsbruck (AT); Markus Oberparleiter, Rum (AT); Werner Lindenthaler, Oberperfuss (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 94 days.

(21) Appl. No.: 15/683,858

(22) Filed: Aug. 23, 2017

(65) Prior Publication Data

US 2017/0348523 A1 Dec. 7, 2017

Related U.S. Application Data

(63) Continuation-in-part of application No. PCT/US2016/018858, filed on Feb. 22, 2016.
(Continued)

(51) Int. Cl.
*A61N 1/05* (2006.01)
*A61N 1/36* (2006.01)
*A61N 1/30* (2006.01)

(52) U.S. Cl.
CPC ........ *A61N 1/0558* (2013.01); *A61N 1/0539* (2013.01); *A61N 1/36017* (2013.01); *A61N 1/36114* (2013.01); *A61N 1/306* (2013.01)

(58) Field of Classification Search
CPC ...... A61N 1/05; A61N 1/0539; A61N 1/0558; A61N 1/36; A61N 1/36017; A61N 1/36114
See application file for complete search history.

(56) References Cited

U.S. PATENT DOCUMENTS 3,902,501 A 9/1975 Citron et al.
5,246,014 A * 9/1993 Williams ................. A61N 1/05
607/122

(Continued)

OTHER PUBLICATIONS

International Searching Authority, International Search Report—International Application No. PCT/US2016/018858, dated Apr. 22, 2016 together with the Written Opinion of the International Searching Authority, 13 pages.

*Primary Examiner* — Christopher A Flory
(74) *Attorney, Agent, or Firm* — Sunstein Kann Murphy & Timbers LLP

(57) ABSTRACT

An implantable neural tissue electrode assembly includes a cylindrical electrode lead with at least one electrode contact on the outer surface of the electrode lead. An active distal end fixation anchor is located at the distal end of the electrode lead and is adapted to fasten to adjacent tissue by rotation in a fastening direction. A passive rear fixation anchor is located on the outer surface of the electrode lead offset a longitudinal distance back from the distal end and has at least one curved blade with a blade tip directed away from rotation in the fastening direction. The rear fixation anchor is adapted to permanently fasten to adjacent tissue by rotation opposite to the fastening direction so that the blade tip cuts into the adjacent tissue, and the electrode assembly is adapted such that physiological induced strains are distributed along the electrode lead.

5 Claims, 2 Drawing Sheets

Related U.S. Application Data

(60) Provisional application No. 62/119,861, filed on Feb. 24, 2015.

(56) References Cited

U.S. PATENT DOCUMENTS

| | | | | |
|---|---|---|---|---|
| 5,300,107 | A * | 4/1994 | Stokes | A61N 1/057 607/126 |
| 5,693,081 | A | 12/1997 | Fain et al. | |
| 6,156,046 | A * | 12/2000 | Passafaro | A61B 17/221 128/898 |
| 6,599,311 | B1 * | 7/2003 | Biggs | A61B 17/00234 128/898 |
| 2004/0078054 | A1 * | 4/2004 | Biggs | A61B 17/00234 606/232 |
| 2007/0112384 | A1 * | 5/2007 | Conlon | A61B 17/0401 606/232 |
| 2009/0082828 | A1 | 3/2009 | Ostroff | |
| 2010/0211149 | A1 | 8/2010 | Morgan et al. | |
| 2010/0324644 | A1 * | 12/2010 | Levi | A61B 5/6882 607/133 |
| 2011/0307043 | A1 * | 12/2011 | Ollivier | A61N 1/0587 607/127 |
| 2012/0116489 | A1 * | 5/2012 | Khairkhahan | A61N 1/375 607/127 |
| 2013/0323253 | A1 | 12/2013 | Barker et al. | |
| 2015/0039070 | A1 | 2/2015 | Kuhn et al. | |
| 2015/0272586 | A1 * | 10/2015 | Herman | A61B 17/0401 606/151 |
| 2015/0306378 | A1 * | 10/2015 | Schmidt | A61N 1/059 600/424 |
| 2016/0310732 | A1 * | 10/2016 | Beck | A61N 1/36003 |

\* cited by examiner

ACTIVE FIXATION OF NEURAL TISSUE ELECTRODES

This application is a continuation-in-part of Patent Cooperation Treaty Application PCT/US2016/018858, filed Feb. 22, 2016, which in turn claims priority from U.S. Provisional Patent Application 62/119,861, filed Feb. 24, 2015, both of which are incorporated herein by reference in their entireties.

TECHNICAL FIELD

The present invention relates to an implantable neural tissue electrode arrangement that encompasses two fixation mechanisms.

BACKGROUND ART

Some medical treatment devices are based on applying electrical stimulation signals to target neural tissue. Typically a peripheral nerve receives the electrical stimulation from an implantable electrode that is inserted into nearby host tissue. It is important that such an implantable electrode be securely fixed at its implantation site to avoid post-surgical migration, which can reduce the electrode's ability to adequately stimulate the nerve.

Existing implantable electrodes, such as the pacing electrodes made by Medtronic, Boston Scientific, St. Jude, Biotronik USA and Osypka, use either active fixation mechanisms such as a helical screw fixation tips, or passive fixation mechanisms such silicone/polyurethane tines along the length of the electrode lead or at the distal tip. For example, U.S. Patent Publication 20120323253 by Garai describes an implantable electrode array with an active anchor tip that initially is retracted within the electrode lead. Then during implantation surgery, the anchor tip can be extended outside the rest of the lead for tissue fixation.

U.S. Pat. No. 5,693,081 by Fain describes an implantable electrode with a hook fixation element that is both active and passive. The fixation hook is located approximately back from the distal tip of the lead and is adapted to move out away from the electrode body to stick out at an angle of 90 degrees and then be rotated with the lead to hook into the adjacent tissue. The Fain arrangement is quite complicated and given the diameter of an actual electrode lead may not be feasible.

SUMMARY

Embodiments of the present invention are directed to implantable neural tissue electrode arrangements. A cylindrical electrode lead has an outer surface and a distal end. There is at least one electrode contact on the outer surface of the electrode lead for electrical interaction with adjacent tissue. An active distal end fixation anchor is located at the distal end of the electrode lead and is adapted to fasten to adjacent tissue by rotation in a fastening direction. A passive rear fixation anchor is located on the outer surface of the electrode lead offset a longitudinal distance back from the distal end and has at least one curved blade with a blade tip directed away from rotation in the fastening direction. The rear fixation anchor is adapted to permanently fasten to adjacent tissue by rotation opposite to the fastening direction so that the blade tip cuts into the adjacent tissue, and the electrode assembly is adapted such that physiological induced strains are distributed along the electrode lead.

In specific embodiments, there may also be a surgical insertion holder that fits coaxially around a portion of the electrode lead that includes the rear fixation anchor and leaves the distal end fixation anchor exposed for fastening. The surgical insertion holder is adapted for retraction after fastening of the distal end fixation anchor to expose the rear fixation anchor for fastening.

The rear fixation anchor may include multiple curved blades. The rear fixation anchor may be connected to the outer surface of the electrode lead by a conical hull connector. At least one of the fixation anchors may be a stimulation electrode for electrical stimulation of adjacent tissue, and/or a sensing electrode for sensing electrical activity in adjacent tissue. The adjacent tissue may specifically be laryngeal tissue or cardiac tissue.

DETAILED DESCRIPTION

Various embodiments of the present invention are directed to implantable neural tissue electrode arrangements—e.g. cardiac pacemakers or laryngeal pacemakers—By distributing the different fixation elements to different locations on the electrode lead, strains induced on the lead by physiological forces are shared by the anchoring elements and distributed along the electrode lead.

Figure 1:
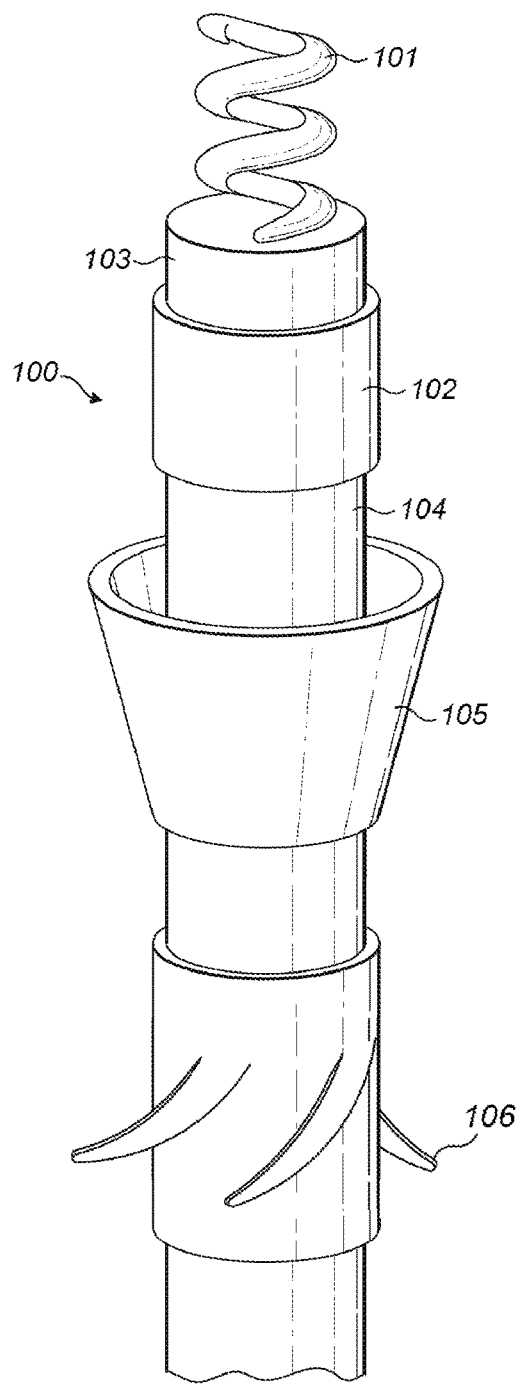
FIG. 1 shows an implantable neural tissue electrode assembly according to an embodiment of the present invention.

FIG. 1 shows an implantable neural tissue electrode arrangement 100 that includes a cylindrical electrode lead 104 with at least one electrode contact 102 on its outer surface for electrical interaction with adjacent tissue. For example, the electrode contact 102 may be a stimulation electrode for electrical stimulation of adjacent tissue, and/or a sensing electrode for sensing electrical activity in adjacent tissue. In the embodiment shown in FIG. 1, the electrode contact 102 is located just slightly back as from distal end 103 of the electrode lead 104. The specific location may be different in other specific embodiments, for example, on the distal end 103 or further back at a location along the length of the electrode lead 104.

An distal end fixation anchor 101 is located at the distal end 103 of the electrode lead 104 and is adapted to fasten to adjacent tissue by rotation in a fastening direction. For example, the distal end fixation anchor 101 may specifically be an attachment screw or a helically wound spring element. The distal end fixation anchor 101 may be a purely structural element, or in some embodiments it may also act as an electrode contact for electrical interaction with the tissue it is fastened to, acting as a stimulation electrode for electrical stimulation of tissue adjacent to the distal end 103, and/or a sensing electrode for sensing electrical activity in tissue adjacent to the distal end 103.

A rear fixation anchor 106 is located on the outer surface of the electrode lead 104 offset a longitudinal distance back from the distal end 104. The rear fixation anchor 106 has one or more curved blades with blade tips directed away from rotation in the fastening direction. The rear fixation anchor 106 is adapted to permanently fasten to adjacent tissue by rotation opposite to the fastening direction of the distal end fixation anchor 101. So after the distal end fixation anchor 101 is screwed into the tissue at its fastening location, it is unscrewed slightly back in the opposite direction to fasten the rear fixation anchor 106 to the tissue adjacent to it.

In the embodiment shown in FIG. 1, the rear fixation anchor 106 comprises multiple curved blades adapted for fastening to adjacent tissue by rotation opposite to the fastening direction of the distal end fixation anchor 101. In other embodiments, the rear fixation anchor 106 may have just a single curved blade or a single helical ridged tine. The embodiment shown in FIG. 1 also includes a conical hull connector 105 that may be attached onto the electrode lead 104 (e.g., crimped on by the surgeon during attachment surgery) that limits how far the rear fixation anchor 106 may move towards the distal end 103, but which allows positioning adjustment back along the electrode lead 104 in the other direction. In other specific embodiments, the rear fixation anchor 106 may be permanently and immovably affixed to a specific location on the electrode lead 104. And like the distal end fixation anchor 101, the rear fixation anchor 106 may be a purely structural element, or in some embodiments it may also act as an electrode contact for electrical interaction with the tissue it is fastened to, acting as a stimulation electrode for electrical stimulation of tissue adjacent to the distal end 103, and/or a sensing electrode for sensing electrical activity in tissue adjacent to the distal end 103.

Figure 2A:
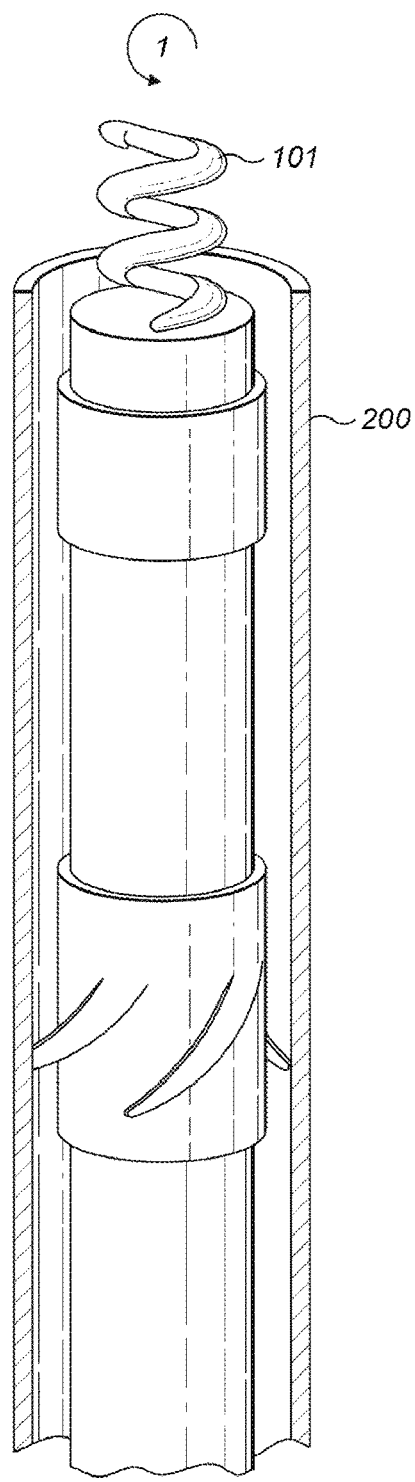
FIGS. 2 A-B show the implantable neural tissue electrode with a surgical insertion holder according to an embodiment of the present invention.
Figure 2B:
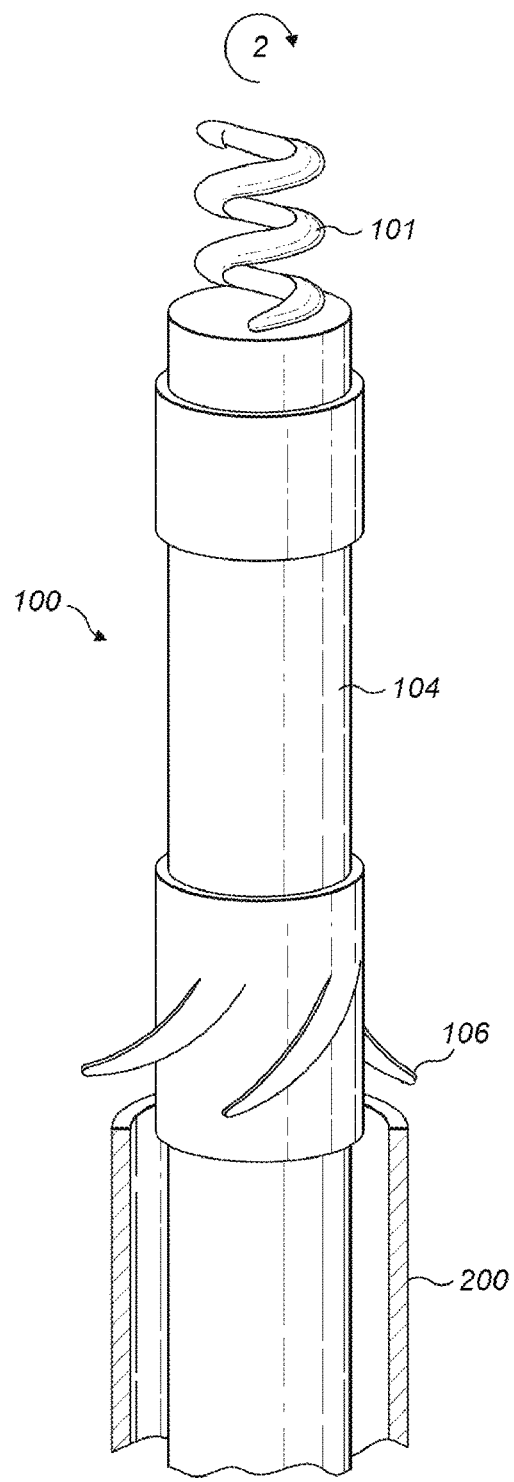

FIGS. 2 A-B show an implantable neural tissue electrode 100 with a surgical insertion holder 200 according to an embodiment of the present invention. As shown in FIG. 2A, for surgical insertion of the electrode 100 into the patient, the surgical insertion holder 200 fits coaxially around a portion of the electrode lead 104 that includes the proximal fixation anchor 106 and leaves the distal end fixation anchor 101 exposed for fastening. When the distal end fixation anchor 101 reaches the fixation site, the surgeon rotates the electrode 100 in the fastening direction ("1") to securely fasten it. The as shown in FIG. 2B, the surgical insertion holder 200 is retracted back to expose the rear fixation anchor 106 for fastening by rotating the electrode back a bit by rotation opposite to the fastening direction ("2").

The electrode arrangement 100 and the distributed locations of the distal end fixation anchor 101 and the rear fixation anchor 106 distribute the physiologically-induced strains that result from fastening of the fixation anchors to adjacent tissue and distribute those mechanical strains along the electrode lead 104 between the fixation anchors.

Electrode arrangements such those described have a relatively simple design without multicomponent substructures that can encompass a complex internal assembly of moving mechanical parts. This makes it possible to such arrangements for commercial manufacture instead of being a mere concept that cannot be manufactured on the required commercial scale and which cannot be used with electrode lead dimensions which are small enough in order to be considered for implantation.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable neural electrode assembly comprising:
   a cylindrical electrode lead with an outer surface and a distal end;
   at least one electrode contact on the outer surface of the electrode lead for electrical interaction with adjacent tissue;
   an active distal end fixation anchor at the distal end of the electrode lead adapted to fasten to adjacent tissue by rotation in a fastening direction;
   a rear fixation anchor on the outer surface of the electrode lead offset from the distal end and including plurality of tines adapted to fasten to adjacent tissue by rotation opposite to the fastening direction; and
   a conical hull connector on the outer surface of the electrode lead between the distal end and the rear fixation anchor and adapted to allow back positioning adjustment of the electrode lead while limiting how far the rear fixation anchor may move towards the distal end;
   wherein the electrode assembly is adapted such that physiological induced strains are distributed along the electrode lead.

2. The electrode assembly according to claim 1, further comprising:
   a surgical insertion holder fitting coaxially around a portion of the electrode lead including the rear fixation anchor and leaving the distal end fixation anchor exposed for fastening;
   wherein the surgical insertion holder is adapted for retraction after fastening of the distal end fixation anchor to expose the rear fixation anchor for fastening.

3. The electrode assembly according to claim 1, further comprising:
   a second distal electrode on the outer surface of the electrode lead at the distal end near the distal end fixation anchor for electrical interaction with adjacent tissue.

4. The electrode assembly according to claim 1, wherein at least one of the fixation anchors is a stimulation electrode for electrical stimulation of adjacent tissue.

5. The electrode assembly according to claim 1, wherein at least one of the fixation anchors is a sensing electrode for sensing electrical activity in adjacent tissue.

* * * * *